United States Patent
Gerdes

(10) Patent No.: US 6,267,779 B1
(45) Date of Patent: Jul. 31, 2001

(54) METHOD AND APPARATUS FOR THERAPEUTIC LASER TREATMENT

(75) Inventor: Harold M. Gerdes, Peninsula, OH (US)

(73) Assignee: MedeLaser, LLC, West Palm Beach, FL (US)

( * ) Notice: Subject to any disclaimer, the term of this patent is extended or adjusted under 35 U.S.C. 154(b) by 0 days.

(21) Appl. No.: 09/281,443

(22) Filed: Mar. 29, 1999

(51) Int. Cl.$^7$ ................................................. A61N 5/00
(52) U.S. Cl. .................................... 607/89; 606/3
(58) Field of Search ............................ 606/2, 3, 9–15; 607/88, 89

(56) References Cited

U.S. PATENT DOCUMENTS

| | | |
|---|---|---|
| 3,769,963 | 11/1973 | Goldman et al. . |
| 3,900,034 | 8/1975 | Katz et al. . |
| 4,069,823 | 1/1978 | Isakov et al. . |
| 4,396,285 | 8/1983 | Presta et al. . |
| 4,573,465 | 3/1986 | Sugiyama et al. . |
| 4,573,467 | 3/1986 | Rich et al. . |
| 4,640,283 | 2/1987 | Sawa et al. . |
| 4,669,839 | 6/1987 | Muchel . |
| 4,671,285 | 6/1987 | Walker . |
| 4,724,835 | 2/1988 | Liss et al. . |
| 4,854,320 | 8/1989 | Dew et al. . |
| 4,930,504 * | 6/1990 | Diamantopoulos et al. ............ 606/3 |
| 4,931,053 | 6/1990 | L'Esperance, Jr. . |
| 4,966,144 | 10/1990 | Rochkind et al. . |
| 4,984,242 | 1/1991 | Scifres et al. . |
| 5,002,051 | 3/1991 | Dew et al. . |
| 5,021,452 | 6/1991 | Labbe et al. . |
| 5,049,147 | 9/1991 | Danon . |
| 5,050,597 | 9/1991 | Daikuzono . |

(List continued on next page.)

FOREIGN PATENT DOCUMENTS

PCT/US93/
04123   11/1993   (WO) .

OTHER PUBLICATIONS

Bolognami et al., "Effects of GaAs Pulsed Lasers on ATP Concentration and ATPase Activity In Vitro and In Vivo," International Cong. On Lasers in Medicine and Surgery, p. 47 (1985).

Karu and Letokhov, "Biological Action of Low–Intensity Monochromatic Light in the Visible Range," *Laser Photobiology and Photomedicine*, ed. Martellucci, pp. 57–66 (Plenum Press 1985).

Passarella et al., "Certain Aspects of Helium–Neon Laser Irradiation on Biological Systems in Vitro," *Ibid* at pp. 67–74.

"Low–Intensity Laser Reduces Arthritis Symptoms" by Pfieiffer in the *Journal of Clinical Laser Medicine & Surgery*, vol. 10, No. 6, (1992).

In a research report by Beckerman et al. entitled: "The Efficacy of Laser Therapy for Musculoskeletal and Skin Disorders: A Criteria–Based Meta–analysis of Randomized Clinical Trials", *Physical Therapy*, vol. 72, No. 7, Jul., 1992.

*Primary Examiner*—Michael Peffley
(74) *Attorney, Agent, or Firm*—Sean M. Casey

(57) ABSTRACT

The therapeutic laser apparatus includes at least two wands connected to a controller and radiation source via fiber optic cables. The controller and source include at least two infrared wavelength solid-state diode ("SSD") lasers and at least two visible wavelength SSD aiming lasers. The apparatus further includes a combiner configured to maintain the electromagnetic radiation from one infrared SSD laser coincident with one visible light SSD aiming laser. In the method according to the invention, the visible light SSD aiming laser is used as a pointer so that an operator can position the wands adjacent to the skin of a mammal whereby the beams of infrared treatment lasers intersect at a region inside the body of the mammal.

30 Claims, 8 Drawing Sheets

U.S. PATENT DOCUMENTS

| | | |
|---|---|---|
| 5,112,328 | 5/1992 | Toboada et al. . |
| 5,147,349 * | 9/1992 | Johnson et al. .......................... 606/4 |
| 5,150,704 * | 9/1992 | Tatebayashi et al. .................... 606/3 |
| 5,161,526 | 11/1992 | Hellwing et al. . |
| 5,196,004 | 3/1993 | Sinofsky . |
| 5,259,380 | 11/1993 | Mendes et al. . |
| 5,290,273 | 3/1994 | Tan . |
| 5,312,396 | 5/1994 | Feld et al. . |
| 5,346,488 | 9/1994 | Prince et al. . |
| 5,409,482 | 4/1995 | Diamantopoulos . |
| 5,445,146 | 8/1995 | Bellinger ................................ 607/89 |
| 5,464,436 | 11/1995 | Smith . |
| 5,520,679 | 5/1996 | Lin . |
| 5,527,350 | 6/1996 | Grove et al. . |
| 5,540,676 * | 7/1996 | Freiberg .................................... 606/3 |
| 5,616,140 | 4/1997 | Prescott . |
| 5,707,403 | 1/1998 | Grove et al. . |
| 5,755,752 | 5/1998 | Segal . |
| 5,951,596 | 9/1999 | Bellinger . |
| 5,993,442 * | 11/1999 | Omori .................................... 606/10 |

\* cited by examiner

METHOD AND APPARATUS FOR THERAPEUTIC LASER TREATMENT

TECHNICAL FIELD

The invention is directed to an apparatus and a method for applying laser beam energy in the treatment of medical conditions. More specifically, the present invention is concerned with an apparatus that uses wands emitting visible laser beam energy and invisible infrared laser beam energy. The method of the invention comprises positioning the wands over the patient in a manner such that the infrared radiation from the wands intersects within the body of the animal being subjected to therapy.

BACKGROUND OF THE INVENTION

The application of laser beam energy in the treatment of medical conditions has been investigated since the early 1970's. Numerous investigators have demonstrated that the application of low power laser beam energy on the order of 1 to 100 milliwatts and at varying wave lengths (e.g., 700–1100 nanometers) ("nm") is effective in the treatment of various medical conditions. Low-level laser beam energy has been shown to enhance wound healing and reduce the development of scar tissue after surgical procedures. Such energy has also been shown to relieve stiff joints and promote the healing of injured joints, stimulate the body's ability to heal fractures and large contusions, as well as enhancing the healing of decubitus ulcers.

Medical and dental applications for low level laser beam energy of varying wave lengths also include pain control, nerve stimulation, reduction of edema, reduction of inflammation, arthritis, muscle and tendon injuries, and stimulation of the body's neurohormone system. Other applications have demonstrated increased activity in cells specifically connected with the immune system and antigen response.

The mechanisms of how the tissues of a mammal respond to low power laser beam energy is not well elucidated or understood. Therapeutic laser treatments of humans, animals, and biological tissues have been commonly referred to as "photobiostimulation" treatments. Suggestions have been made that the process of photobiostimulation accelerates the initial phase of wound healing by altering the levels of prostaglandins. It has also been suggested the laser beam energy increases ATP synthesis, accelerates collagen synthesis, and increases the ability of immune cells to ward off invading pathogens. See, e.g., Bolognami et al., "Effects of GaAs Pulsed Lasers on ATP Concentration and ATPase Activity In Vitro and In Vivo," *International Cong. On Lasers in Medicine and Surgery*, p. 47 (1985); Karu and Letokhov, "Biological Action of Low-Intensity Monochromatic Light in the Visible Range," *Laser Photobiology and Photomedicine*, ed. Martellucci, pp. 57–66 (Plenum Press 1985); Passarella et al., "Certain Aspects of Helium-Neon Laser Irradiation on Biological Systems in Vitro," Ibid at pp. 67–74.

Conventional low power (less than 100 milliwatts) laser therapeutic devices generally comprise a hand held probe with a single laser beam source, or a large stationary table console with attached probes powered by a conventional fixed power supply. A common laser beam source is the laser diode. Laser diodes are readily available in varying power and wavelength combinations. Large probes containing multiple laser diodes are also known.

BACKGROUND ART

Isakov et al., in U.S. Pat. No. 4,069,823, disclose an apparatus for laser therapy including one or several lasers, a light guide and a focusing barrel wherein there are at least two platforms for transverse and longitudinal travel so that tissue can be dissected. The patent also discloses the use of a visible light beam that coincides with the laser beam thus allowing the surgeon to accurately aim the invisible laser beam to the required point. $CO_2$ lasers with wavelengths in the area of 1060 nm are employed. This patent also suggests laser beam densities of up to $10^5$ watts per square centimeter.

Kanazawa et al. disclose in U.S. Pat. No. 4,640,283, a method of curing athlete's foot by laser beam irradiation. This patent discloses the use of a laser such as a $CO_2$ laser or a YAG laser that emits a laser beam in the infrared region having a wavelength of 700 nm or more. Energy levels are disclosed as two joules per centimeter squared or more for a period of ten milliseconds or less. This patent does not suggest or disclose the use of an apparatus including at least two wands for the laser therapy of medical conditions such as arthritis and bursitis.

Muchel in U.S. Pat. No. 4,699,839 discloses an optical system for therapeutic use of laser light. The Muchel instrument provides for combined observation of and laser treatment of a portion of a human body, such as an eye. This patent discloses the construction of main objective lenses within certain parameters adapted to combine laser therapy radiation from multiple sources. One source emits radiation having a wavelength of, for example, 1064 nm. A second source emits laser target light radiation having a wavelength of 633 nm. And a third source emits an observation light in the visible spectrum range of from 480 nm to 644 nm.

U.S. Pat. No. 4,671,285 to Walker discloses the treatment of human neurological problems by laser photo simulation. This patent relates to a method of treating nerve damage in humans by applying an essentially monochromic light to the skin area adjacent to the damaged nerve region. The inventor describes the use of a helium neon laser (632.5 nm, 1 milliwatt, and 20 hertz) with a fiber optic probe, which is held against the skin of the patient. The inventor also states that irradiation with infrared lasers (1090 nm) had no effect. This reference actually teaches away from the present invention.

Liss et al. teach in U.S. Pat. No. 4,724,835 a therapeutic laser device using a pulsed laser wave. The Liss et al. device uses a gallium aluminum arsenide diode as the source of laser energy which is in the infrared band (wavelength of approximately 900 nm).

U.S. Pat. No. 4,396,285 to Presta et al. relates to a laser system for medical applications that has at least two lasers and a movable concave reflector. One of the beams, an imaging beam, is aligned to impinge the reflector, to reflect therefrom and to impinge on a biological specimen. The reflector is moved until the beam is aligned to impinge the desired location of the specimens. The second beam is also aligned to impinge on the reflector to reflect therefrom and to impinge on the same desired position as that impinged upon by the first beam. The second laser is typically disclosed to be a $CO_2$ laser that generates the second beam having a wavelength of 10.6 microns. The Presta system is disclosed as being useful for microsurgery. This reference does not disclose a laser therapy apparatus wherein the therapeutic radiation and the targeting radiation are merged so as to be coincidental on the surface of the patient's skin and at least two wands for positioning the intersection of the beams within the body of the patient.

U.S. Pat. No. 4,930,504 to Diamantopoulos et al. relates to a device for biostimulation of tissue which comprises an array of monochromic radiation sources of a plurality of wavelengths, preferably at least three different wavelengths. For example, this patent discloses the treatment of patients with a multi-diode biostimulation device having emitted frequencies of 660 nm, 820 nm, 880 nm, and 950 nm. The power levels disclosed are between 5 milliwatts and 500 milliwatts. This patent also discloses obtaining the radiation from a plurality of sources whose outputs are combined to a single emergence region with flexible optic fibers.

Labbé et al., in U.S. Pat. No. 5,021,452, disclose a process for improving wound healing which comprises administering ascorbate or derivatives of ascorbate to the wound site and then irradiating the wound site with a low power laser at a wavelength of about 600 nm to about 1100 nm. This patent discloses that the laser can either be a pulsed or a continuous wave laser with energy outputs ranging from 1.0 millijoule per square centimeter to about 1000 millijoules per square centimeter. This reference does not suggest or disclose an apparatus including at least two wands with a combined beam of therapeutic radiation and targeting radiation which are used to intersect the therapeutic radiation beams within the body of the animal subject to treatment.

U.S. Pat. No. 5,147,349 to Johnson et al. discloses a diode laser device for photocoagulation of the retina. The inventors disclose that the elliptical laser beam is shaped into a circle by an optical system before it is coupled to the fiber optic cable of the delivery system.

Mendes et al. in U.S. Pat. No. 5,259,380, discloses a light therapy system utilizing an array of light emitting diodes which emit non-coherent light in a narrow band width centered at a designated wavelength. The non-coherent light is generated by an array of conventional light emitting diodes with wavelengths in the red or infrared bandwidth. Infrared frequencies in the area of 940 nm, more particularly 880 nm are disclosed.

U.S. Pat. No. 5,409,482 to Diamantopoulos discloses a probe for biomodulation. The probe includes a semiconductor laser and a drive circuit adapted to operate the laser to emit pulses and bursts. The system according to this patent has a laser beam wavelength of 850 nm and a frequency of $352 \times 10^3$ GHz pulsed at 300,000 and additionally modulated at a frequency of from 1 Hz to 2 GHz.

Bellinger in U.S. Pat. No. 5,445,146 describes a laser system for the stimulation of biological tissue that emits radiation with a power of from 100 to 800 milliwatts in either a pulsed or continuous mode. The laser disclosed has a fundamental wavelength of 1064 nm and delivers an energy density of from about one joule per square centimeter to about 15 joules per square centimeter.

Smith in U.S. Pat. No. 5,464,436 discloses a laser therapy apparatus having a wavelength in the range of 800 to 870 nm and more preferably about 830 nm. The laser light is delivered to the afflicted area at a level of about one joule per square centimeter. Smith also suggests that the afflicted area be monitored after the treatment cycle and that treatment steps be repeated to the afflicted area.

U.S. Pat. No. 5,527,350 to Grove et al. discloses a method for treating psoriasis through the use of pulsed infrared laser irradiation. An infrared diode laser is used having a wavelength of 800 nm and a pulse duration in the millisecond range. Energy levels of 5.0 to 50 joules per square centimeter are disclosed.

U.S. Pat. No. 5,616,140 to Prescott discloses a portable laser bandage having one or many lasers or hyper-red light emitting diodes embedded in the bandage. The hyper-red light emitting diodes are disclosed as having wavelengths of about 670 nm.

PCT Application PCT/US93/04123 (WO 93/21993) discloses a low level laser for soft tissue treatment wherein the laser is a Nd:YAG laser, which produces 100 to 800 milliwatts in a pulsed or continuous mode.

In an article entitled;: "Low-Intensity Laser Reduces Arthritis Symptoms" by Pfieiffer in the *Journal of Clinical Laser Medicine & Surgery*, Vol. 10, No. 6, (1992), the author reviews various clinical studies using infrared and red lasers in the treatment of arthritis. This publication makes no disclosure of any specific laser therapy apparatus.

In a research report by Beckerman et al. entitled: "The Efficacy of Laser Therapy for Musculoskeletal and Skin Disorders: A Criteria-Based Meta-analysis of Randomized Clinical Trials", *Physical Therapy*, Vol. 72, No. 7, July, 1992, the authors review the results of 36 randomized clinical trials involving laser therapy. The article concludes that laser therapy seems to have a substantial, specific therapeutic effect. The authors also point out that it is difficult to determine the optimal dosage and treatment schedules. Further, the authors state that the minimal effective dosage in most cases is unknown and that additional questions need to be resolved regarding the optimal wavelength.

While a substantial amount of prior art exists regarding the use of laser therapies in medical conditions, no one has described or suggested an apparatus that comprises at least two wands that emit coincident visible and infrared radiation, wherein the infrared radiation has a wavelength of about 1000 nm. Further, none of the prior investigators have suggested aiming the at least two wands on the surface of the animal being treated so as to have the therapeutic infrared radiation beams intersect inside the animal's body at the site of therapy.

SUMMARY OF THE INVENTION

The therapeutic laser apparatus according to the invention has at least two independent fiber optic laser outputs terminating with wands that have apertures with variable foci. The inventive apparatus also has a main function block wherein the therapeutic infrared radiation is combined with visible laser light and fed into fiber optic cables via couplers. The fiber optic cables transmit the radiation to the wands. The main function block also contains at least two infrared diode lasers and at least two red diode lasers. Through the design of at least two wands, a novel method of therapy has been discovered wherein the patient or caregiver positions the wands in such a manner that the infrared radiation (at about 1000 nm) from the wands intersects at the point of therapy (inside the body), thereby relieving pain and promoting regeneration of tissue.

The amount of energy applied by each wand can range from about 200 to about 2,000 milliwatts. Preferably, the wands are held in each hand of the caregiver at an angle of about 45° relative to the plane of the patient or biological tissue undergoing treatment. The wands are slowly moved in small circular motions favoring positions that allow the beams of laser radiation to intersect in the body at the site of the malady. As will be disclosed below, the apparatus according to the invention can be effectively used to treat joints affected by arthritis and sore muscles. Patients with advanced forms of degenerative arthritis have experienced pain relief and, over time, revitalization of joints previously affected by the disease.

The concept of using heat (infrared radiation) for relief from pain has been practiced for thousands of years. Electrically heated pads have found wide spread use for pain relief on all parts of the human body and this application of infrared radiation for pain relief is usually referred to as diathermy. It has been discovered that the treatment of a patient with a device according to this invention is not simply receiving heat treatment or diathermy. The actual body mechanisms responsible for relief from pain and revitalization of joints and other tissue are not completely understood. The inventors have observed that the treatments with this particular wavelength of about 1,000 nm and the delivery mechanism of at least two wands is especially effective in the treatment of arthritis.

In the main function block, two infrared diode lasers and two red diode lasers are preferably coupled so that these two frequencies are transmitted to the wands via the fiber optic cable. The combined infrared laser radiation and the visible laser light exit the treatment aperture in the wand coincident and therefore provide an excellent aiming mechanism to the caregiver or patient.

The diameter of the fibers used in the apparatus according to the invention may vary over a wide range. However, the diameter is preferably between approximately 400 microns and approximately 800 microns, and more preferably approximately 600 microns, and even more preferably approximately 400 microns. The preferred wavelength of the infrared lasers is between approximately 900 nm and approximately 1100 nm with the best results being obtained with a wavelength of about 980 nm. The low power visible aiming laser component is typically a red diode laser having a wavelength of between about 400 nm and about 700 nm, and more preferably between about 635 nm and about 640 nm. The wavelength of approximately 635–640 nm is preferred because of its high visibility and minimized effect on the human eye. The power output per wand can range from about 0.0001 milliwatts watts to about 2.0 watts.

Thus, there is disclosed a device for biostimulation of biological tissue that includes
  a) at least two radiation sources providing a first wavelength of between approximately 900 nm to approximately 1100 nm;
  b) at least two radiation sources providing a second wavelength of between approximately 400 nm to approximately 700 nm; the radiation sources being arranged such that the first and second wavelengths simultaneously pass through a fiber optic cable;
  c) at least two wands connected to the fiber optic cable and having apertures having variable focus; the wands being arranged such that the coincident first wavelength and second wavelength emitted from each wand pass through a region located within the tissue.

There is further disclosed a method for the treatment of tissue including:
  a) providing at least two infrared laser radiation sources having a wavelength of between approximately 900 nm to approximately 1100 nm;
  b) providing at least two sources of laser radiation having a wavelength between approximately 400 nm and 700 nm;
  c) combining the radiation sources so that the radiation of each source is coincident;
  d) passing the coincident radiation through an optical fiber;
  e) providing at least two wands connected to the optical fiber;
  f) arranging the wands such that the radiation emitted from each of the wands passes through a region located within the tissue; and
  g) exposing the tissue to an irradiation beam for a therapeutically effective period of time.

Also disclosed is a device for photobiostimulation of biological tissue that includes:
  a) a first plurality of treatment radiation sources each providing a respective first radiation beam having a wavelength of between approximately 900 nm and approximately 1100 nm;
  b) a second plurality of aiming radiation sources each providing a respective second radiation beam having a wavelength of between approximately 400 nm and approximately 700 nm; wherein at least one first beam and one second beam concurrently pass through at least one of a plurality of fiber optic cables; and
  c) at least two wands each connected to a different one of the plurality of fiber optic cables, the wands including a collimator configured to establish the focus of the emanating coincident radiation beams; wherein the wands are arranged in an operative position about the tissue such that the radiation beams emitted from each wand simultaneously pass approximately through a region located in the tissue.

The invention also contemplates and discloses a biostimulation device that includes a laser apparatus including a plurality of treatment laser wands each connected to a laser radiation source adapted to emit radiation having a power of between zero and approximately 2.0 watts, an energy of between about 1 joules and about 99 joules, and a wavelength of between approximately 900 nm and 1100 nm; and wherein the laser wands are arranged in an operative position to emit the radiation incident to a region of biological tissue for a therapeutically effective length of time between approximately one and approximately sixty minutes.

Further, a system for photobiostimulation of biological tissue is disclosed. The system includes a controller unit including a power supply and a control panel having operator input devices and output devices;
  the controller unit also including a first plurality of treatment radiation sources each providing a respective first radiation beam having a wavelength of between approximately 900 nm and approximately 1100 nm;
  the controller unit also including a second plurality of aiming radiation sources each providing a respective second radiation beam having a wavelength of between approximately 400 nm and approximately 700 nm; wherein at least one first radiation beam and one second radiation beam concurrently pass through at least one of a plurality of fiber optic cables; and
  at least two wands each connected to a different one of the plurality of fiber optic cables, the wands including a collimator configured to establish the shape of the emanating coincident radiation beams; wherein the wands are arranged in an operative position about the tissue such that the radiation beams emitted from each wand simultaneously pass approximately through a region located in the tissue.

The apparatus according to the invention further includes a controller, a control panel, a power source, and components configured to vary the radiation power and energy, pulse frequency, pulse duration, and duration of the biostimulation treatment.

DETAILED DESCRIPTION OF THE INVENTION

The sources of radiation are preferably semiconductor laser diodes, super-luminous diodes, or light emitting devices, and more preferably are solid-state laser diodes (SSDs). Laser diodes or SSDs produce a beam of light or radiation that is essentially monochromatic, sharply collimated, and coherent. That is, they produce light almost exclusively at one frequency and the light beam has a small angle of divergence. A number of commercially available semiconductor laser diodes exist that are suitable for purposes of the present invention.

Figure 1:
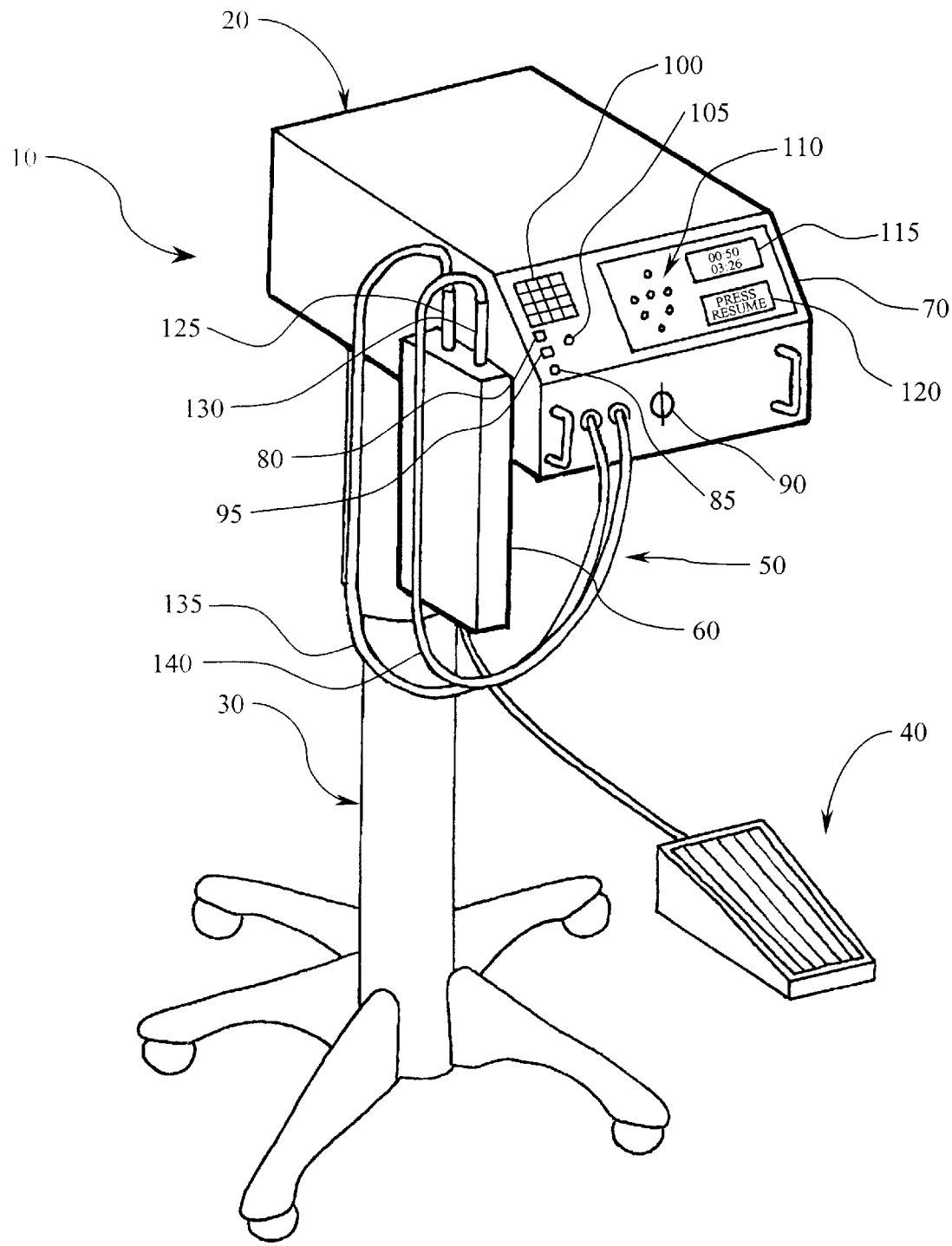
FIG. 1 is a perspective view, in reduced scale, of a biostimulation device incorporating a therapeutic laser apparatus of the present invention.

Referring now to FIG. 1, the preferred embodiment of the present invention is a device 10 for biostimulation of biological tissue that includes a controller cabinet 20 that houses various subcomponents. The cabinet 20 may be mounted to a roller pedestal 30 and it is, in one embodiment, connected to an operator safety pedal 40 and a plurality of laser treatment wands 50 that may be received into a laser radiation shielding receptacle 60. For convenience, the receptacle 60 may be mounted to the cabinet 20. The cabinet is formed with a control panel 70 that includes various input and output devices needed for operating the device 10. Also, although not shown in the various figures, the invention contemplates a room entry-way safety interlock. The safety interlock connects a safety switch mounted to the door-way of the room that houses the therapeutic laser device to the device 10. The safety switch is configured to de-energize all or some of the laser radiation sources upon opening of the door to the room. Inadvertent injury is prevented because laser radiation cannot escape the treatment room. In the preferred embodiment, the entry-way safety interlock is connected to the device 10 and may be portably mounted on any door-way so that the device 10 may be easily moved between a plurality of treatment rooms. Additionally, although pedal 40 is shown in the various figures, the pedal 40 may be accompanied by or entirely replaced by a safety switch mounted on either or both of the laser treatment wands described below.

Figure 2:
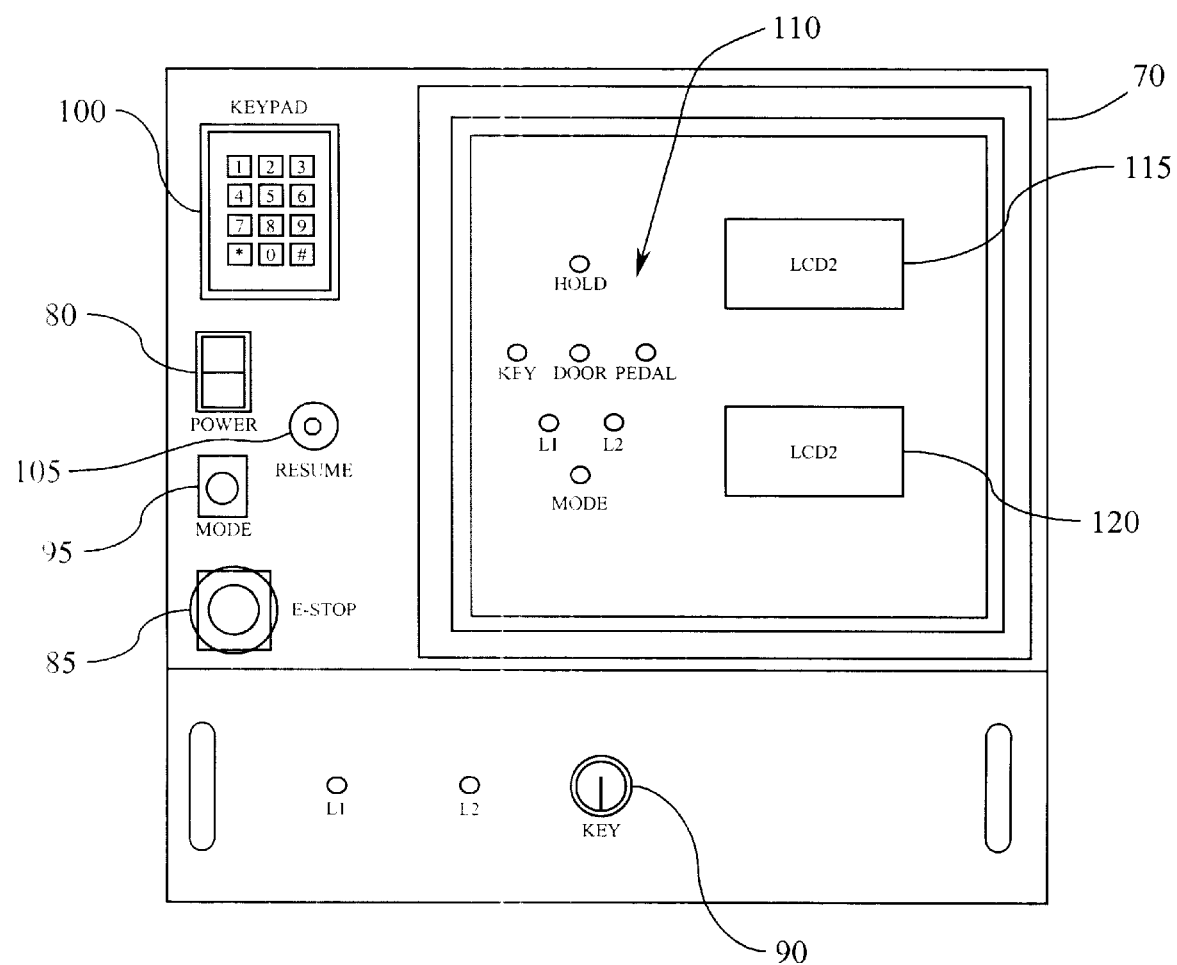
FIG. 2 is a diagrammatic representation of the operation panel of the therapeutic laser apparatus of FIG. 1.

With continued reference to FIG. 1 and also FIG. 2, it can be understood that the control panel 70 further includes a master power switch 80, an emergency stop switch 85, and an operator's safety arming key switch 90. If the arming key is removed from the switch 90, power to laser radiation sources of the device 10 is interrupted to prevent operation of the lasers. Also included on the control panel is a mode switch 95 configured to operate the device 10 in either single or dual laser mode. A numeric entry keypad 100 similar in design to a typical telephone keypad is mounted on the control for configuring the various operating parameters of the device 10 as described in more detail below. The keypad 100 is preferably a hermetically sealed, membrane keypad. A resume switch 105 is also included that is operative to continue interrupted operation.

An output display group on the control panel 70 includes various component status indicators. The indicators include, for example, light emitting diodes (LEDs) 110, liquid crystal alphanumeric displays (LCDs) 115, 120, and audio emitting event buzzers, not shown, each operative to signal component and system status, to prompt the operator for needed input, and to warn of system anomalies and malfunctions. The LCDs are, for example, back-lit, 4 line×20 character displays. The indicators can also indicate the status of the foot pedal 40 and whether any access panels or doors of the main cabinet 20 are open. All access panels or doors of the main cabinet 20 incorporate interlock sensors operative to disconnect power to the laser radiation sources or the device 10, or both, for safety. Additional LEDs 110 and LCDs 115, 120 may also be incorporated to signal that the treatment room door is open or ajar.

Figure 3:
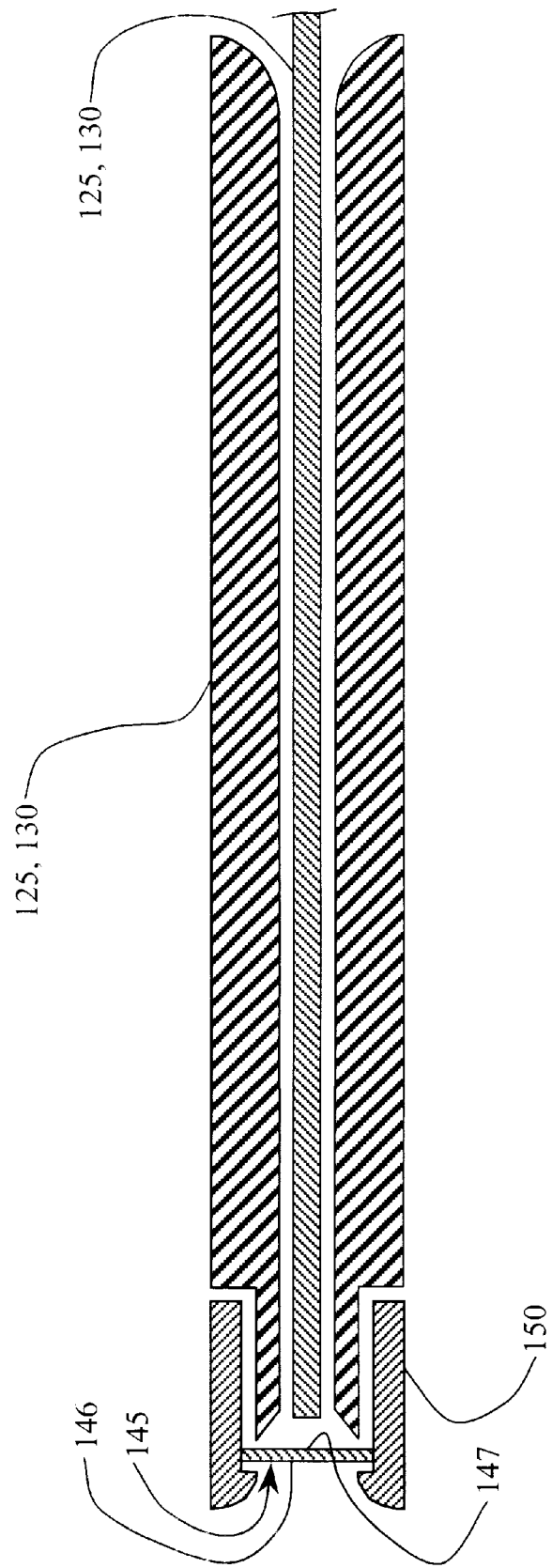
FIG. 3 is a cross-sectional view, in enlarged scale, of the laser wands of FIG. 1.
Figure 4:
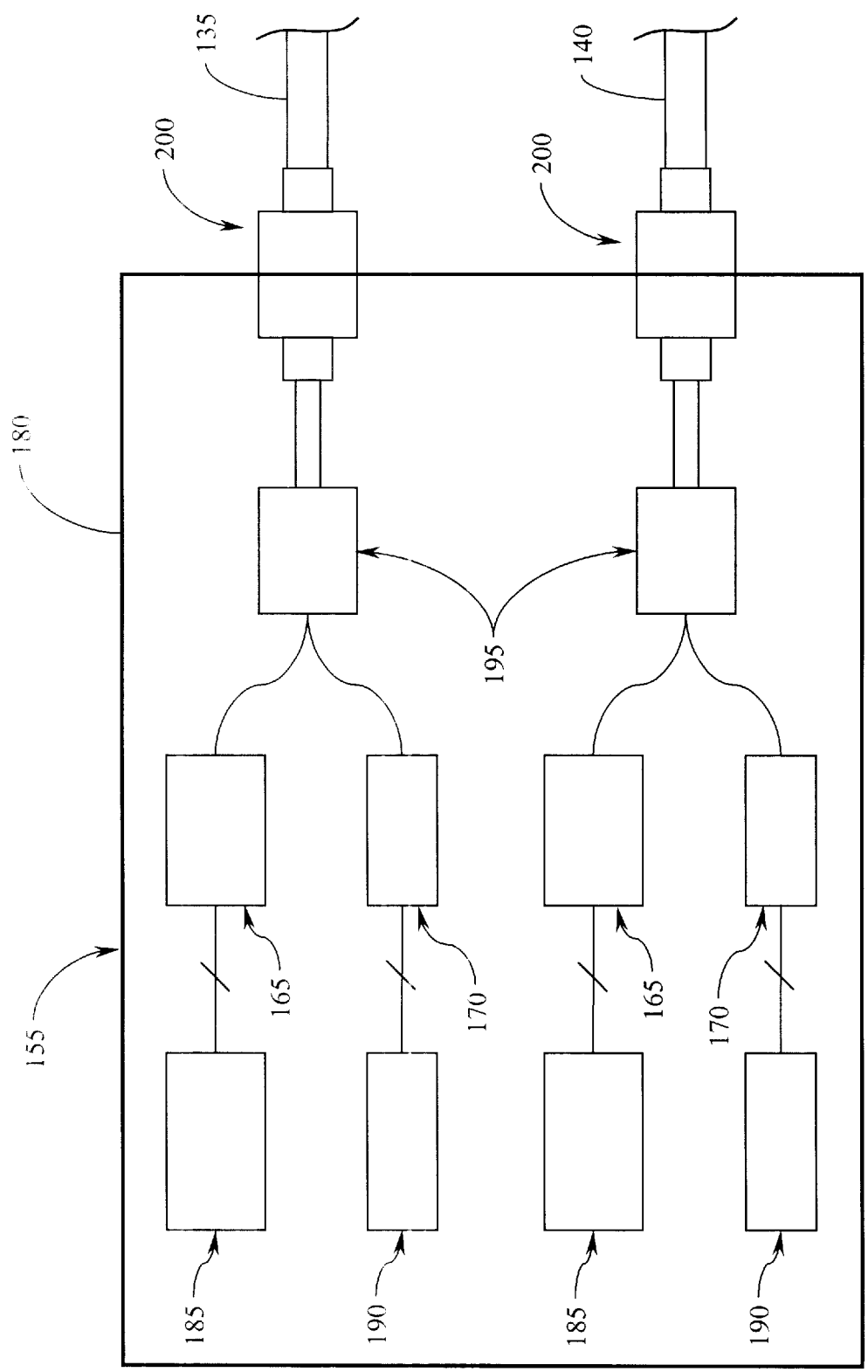
FIG. 4 is a schematic functional representation of the laser radiation sources of the therapeutic laser apparatus of FIG. 1.

Each of the treatment wands 125, 130 of the plurality 50 is connected via fiber optic cables 135, 140 to radiation sources, not shown, inside the cabinet 20. The preferred fiber optic cable for use with the present invention is approximately a 400 micron fiber. Referring now to FIG. 3, it will be observed that each treatment wand 125, 130 incorporates a collimator lens 145 operative to focus the treatment laser beam emitted from the fiber optic cables 135, 140 into the desired beam shape and to project the beam outwardly. In one embodiment of the present invention, the wands each also include an adjustable collimator holder 150 that can be adjusted to vary the shape and focus of the emitted beam. An example of the preferred collimator 145 is an aspheric collimator lens having a focal length of approximately 6.25 millimeters. Typical laser radiation energy losses at each surface of the collimator 145 are, on average, about 4 percent. Therefore, each lens surface 146, 147 preferably includes an anti-reflection coating adapted to minimize the losses at each surface to approximately 0.5 percent. Additionally, the collimator 145 and the holder 150 are arranged to preferably emit a generally circular beam spot having an approximately 4 millimeter diameter. The wands are preferably about 5 to 6 inches in length and are made of aluminum. However, they can be made from any suitable material including, for example, metal, plastic, ceramic, glass, and combinations thereof With reference to FIG. 4, each treatment wand 125, 130 emits laser radiation energy transmitted from at least one of a plurality of laser radiation sources 155 that are preferably contained in a single unit, heat sinked assembly 180. In the preferred embodiment, the laser radiation sources are selected to emit infrared or visible laser radiation, or both. In the preferred embodiment, infrared treatment laser radiation from one source 165 of the plurality 155 is combined with visible laser radiation from another source 170 of the plurality 155 and transmitted into at least one of the fiber optic cables 135, 140.

In this configuration, the positioning of the invisible infrared laser radiation is emitted coincident with the visible laser radiation so that the operator can properly aim the infrared laser radiation emitted from each wand 125, 130 during therapy. Laser radiation sources suitable for use with the present invention include a high-power, Class 4, infrared wavelength SSD laser and a Class 1 or 2, visible wavelength SSD laser available from B. & W. Tek, Inc. of Newark, Del.

U.S.A. Each of these sources is combined into the single unit assembly 180. In the preferred embodiment of the invention, the assembly 180 incorporates a power supply 185, 190 for each laser radiation source 165,170. Also, available from B. & W. Tek is a combiner 195 configured to combine the invisible and visible laser radiation energy into a single fiber optic cable 135, 140 via a releasable, SMA 906 compliant, fiber optic coupler 200.

Each of the infrared treatment laser radiation sources 165 is adapted to emit Class 4 infrared treatment laser radiation with an adjustable power of preferably between approximately zero and approximately 10.0 watts, and more preferably between approximately zero and approximately 5.0 watts, and even more preferably between approximately zero and approximately 2.0 watts. This capability assures an emitted infrared treatment laser radiation power at the treatment end of each of the wands 125, 130 of preferably between about zero and approximately 2.0 watts. These parameters account for many variables including the ability of the biological tissue to absorb radiation and the unavoidable power losses in the combiner 195, coupler 200, cables 135, 140, and wands 125, 130. Additionally, each of the infrared treatment laser radiation sources 165 are further configured to emit laser radiation having a wavelength preferably between approximately 900 nanometers ("nm") and approximately 1100 nm, and more preferably approximately 980 nm.

Each of the visible laser radiation sources 170 are preferably configured to emit Class 1 to Class 2 laser radiation with either a fixed or adjustable power of approximately 0.5 milliwatts to approximately 6 milliwatts. This capability assures a visible emitted laser radiation power at the treatment end of each of the wands 125, 130 including the unavoidable power losses in the combiner 195, coupler 200, cable 135, 140, and wands 125, 130. Additionally, each of the visible laser radiation sources 170 is also configured to emit radiation having a wavelength preferably between approximately 400 nm to approximately 700 nm, and more preferably between about 635 nm and about 640 nm.

Although only four laser radiation sources 165, 170 are described above and shown in FIG. 4, the plurality 155 contemplates any number of greater and fewer laser sources configured to emit laser radiation at various power levels and wavelengths for one or more wands or therapeutic treatment applicators or emitters. Additionally, although a circular beam shape of approximately 4 mm is disclosed, a wide variety of feathered, diffused, Fresnel, traced, and other types of spread-out patterns are also suitable for use with the present invention. Such patterns also include rectangular, square, oval, and elliptical patterns, as well as predetermined or random movably scanned or traced beam patterns that are adapted to be spread over a selected region or to trace a specific shape or pattern.

Figure 5:
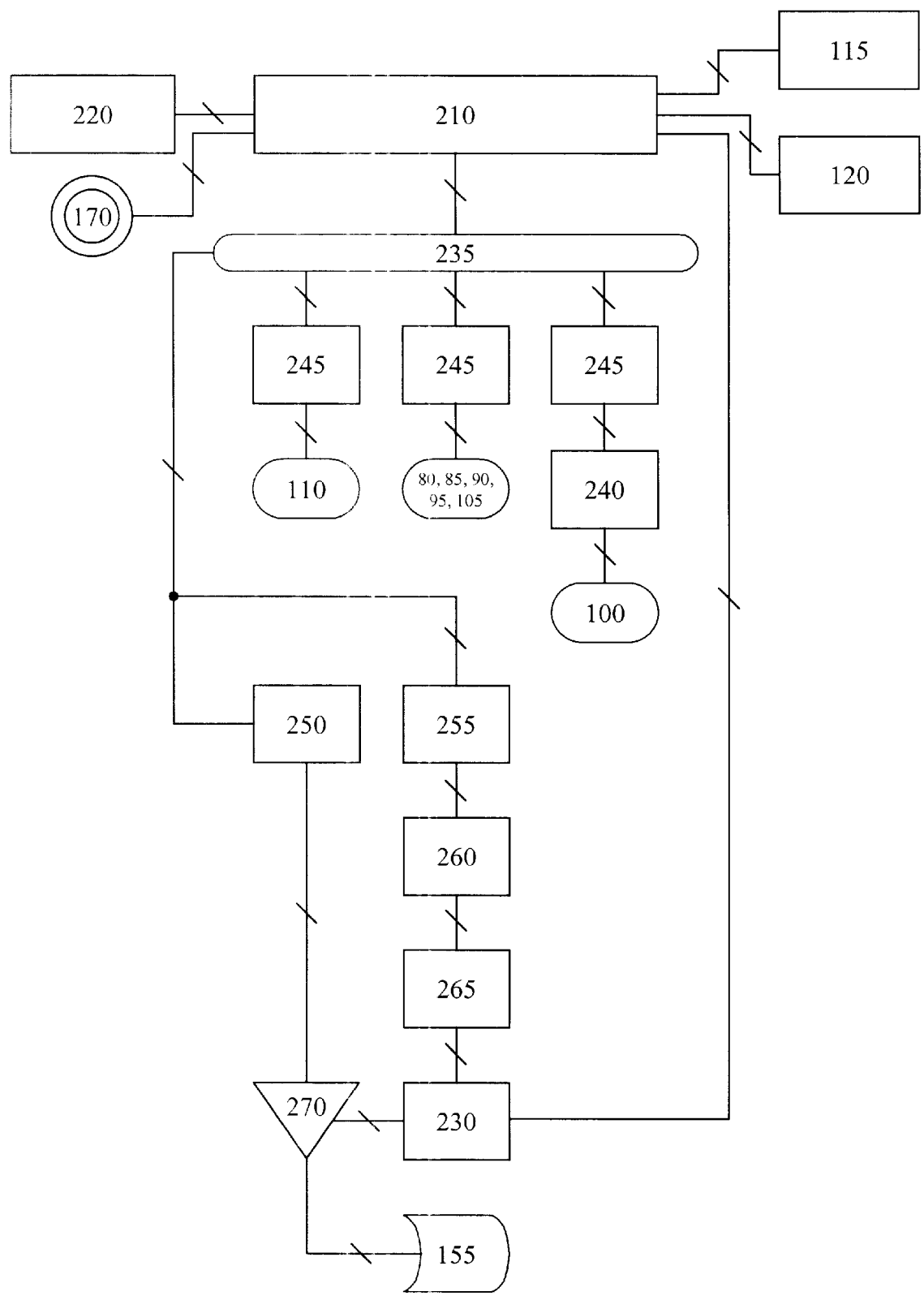
FIG. 5 is a schematic functional representation of the major sub-components of the therapeutic laser apparatus of FIG. 1.

With reference to FIG. 1 and the block-diagram schematic represented in FIG. 5, the cabinet 20 incorporates various components interconnected with the control panel 70, the laser radiation sources 155 and wands 125, 130, and the foot pedal 40. The components are configured to control the laser radiation sources 165, 170 for therapeutically effective biostimulation of human, animal, and experimental biological tissues. The device 10 includes a single board computer or controller component 210 that is preprogrammed to control each of the other components and functions of the device 10. One example of a suitable controller 210 is the BASIC Stamp II-SX microcontroller and accompanying chip set from Parallax, Inc., of Rocklin, Calif. The controller 210 electronically communicates with a year 2000 compliant clock such as the Pocket Watch B 220 from Solutions[3] (Solutions Cubed) of Chico, Calif., the audio emitter 170, and the LCDs 115, 120. The controller 210 communicates directly with the laser radiation sources 155 through both a multiplexer interface circuit 230 and an information bus interface circuit 235 such as, for example, the I$^2$C serial bus chip set available from Philips Semiconductors of Sunnyvale, Calif. The keypad 100 electronically communicates with the controller 210 via the bus 235 through a decoder circuit 240 and an 8-bit, quasi-bidirectional expander 245. The indicators 110 and the switches 80, 85, 90, 95, 105 also communicate with the controller 210 via the bus 235 through converters 245. An example of a decoder circuit or chip set 240 suitable for use in the present invention is the model 74HC147 chip available from Harris Semiconductor, Inc. of Palm Bay, Fla. An example of a suitable 8-bit, quasi-bidirectional expander circuit or chip set 245 is the model PCF8574 I$^2$C bus compatible chip set available from Philips Semiconductors.

The controller 210 also communicates with and controls the power, duration, pulse frequency, and pulse width or duty cycle of the laser radiation sources 155 through the bus 235, and through various interface circuits. The primary interface circuit stage includes dual, independently operable 8-bit digital-to-analog converters 250, 255. The first converter 250 is configured to provide a controlled output voltage of between approximately zero volts and approximately 1.25 volts and is adapted to drive the power output of the laser sources 155. The second converter 255 is configured to provide a controlled output of between approximately zero volts and 5 volts and is adapted to drive a laser pulse frequency and duty cycle interface circuit. One example of an adequate converter 250, 255 is the model PCF8591 I$^2$C bus compatible converter also available from Phillips Semiconductors.

The converter 255 drives a voltage controlled oscillator ("VCO") 260 configured to output a signal modulated between approximately 100 Hertz ("Hz") and 1,000 Hz. A suitable VCO 260 is the model AD654 VCO available from Analog Devices, Inc. of Norwood, Mass. The VCO 260 electronically communicates with a pulse width modulator ("PWM") circuit or chipset 265 that can be obtained as the model PALCE610 PWM available from Vantis Semiconductor, Inc. (formerly Altera Corporation) of San Jose, Calif. The PWM 265 also communicates with the multiplexer 230, through the laser driver interface 270, and with the laser radiation sources 155.

The controller 210 is programmed to accept operator input from the keypad 100 and the mode switch 95 in response to prompting displayed on the LCDs 115, 120 to obtain the desired power wattage and joule energy levels of the treatment laser radiation sources 165, and to determine whether continuous wave or pulsed wave operation is needed for the desired therapeutic treatment. The controller 210 then computes the duration of time required for application of the therapeutic laser treatment. To accomplish this computation, the controller 210 is programmed, among other aspects, with a power to energy conversion equation that computes time in seconds as a function equal to energy in joules divided by power in watts (T=E×P). If the operator selects pulsed wave operation, the controller 210 prompts for the desired frequency and pulse width or duty cycle. As an example, the operator may select a frequency of one hertz (cycles per second) and a pulse width of 50%. In the preferred embodiment, the pulse width is adjustable between approximately 0.1% and 100%. The controller 210 would then set the laser radiation source or sources to have a pulse frequency of one cycle per second wherein the radiation pulse or pulses are on for 0.5 seconds and off for 0.5 seconds. The controller 210 may also be programmed to adjust the power wattage levels and joule energy levels, as well as the continuous wave or pulsed wave operation of each of the laser radiation sources synchronously or independently. Continuous wave operation is selected by specifying a pulse width or duty cycle of 100%. As an additional safety feature, the controller 210 may be programmed to limit the maximum time of treatment to, for example, 60 minutes. Additionally, the operator may similarly adjust the power level or "brightness" of the visible laser radiation source(s) and to select a pulsed or continuous wave operation.

The controller 255 also preferably electronically communicates with a hardware reset switch and a serial port interface circuit, not shown, but incorporated into the back plane of the cabinet 20. The hardware-reset switch is preferably operative to perform a low-level system reset in the event of hardware or software anomalies in device 10. The serial port is configured to communicate with the controller 210 for purposes of external software control of the device 10 or its components, e.g., the lasers, or both. Also, the serial port can be configured to allow remote monitoring of device diagnostics, and to upload software upgrades to the device 10.

Figure 6A:
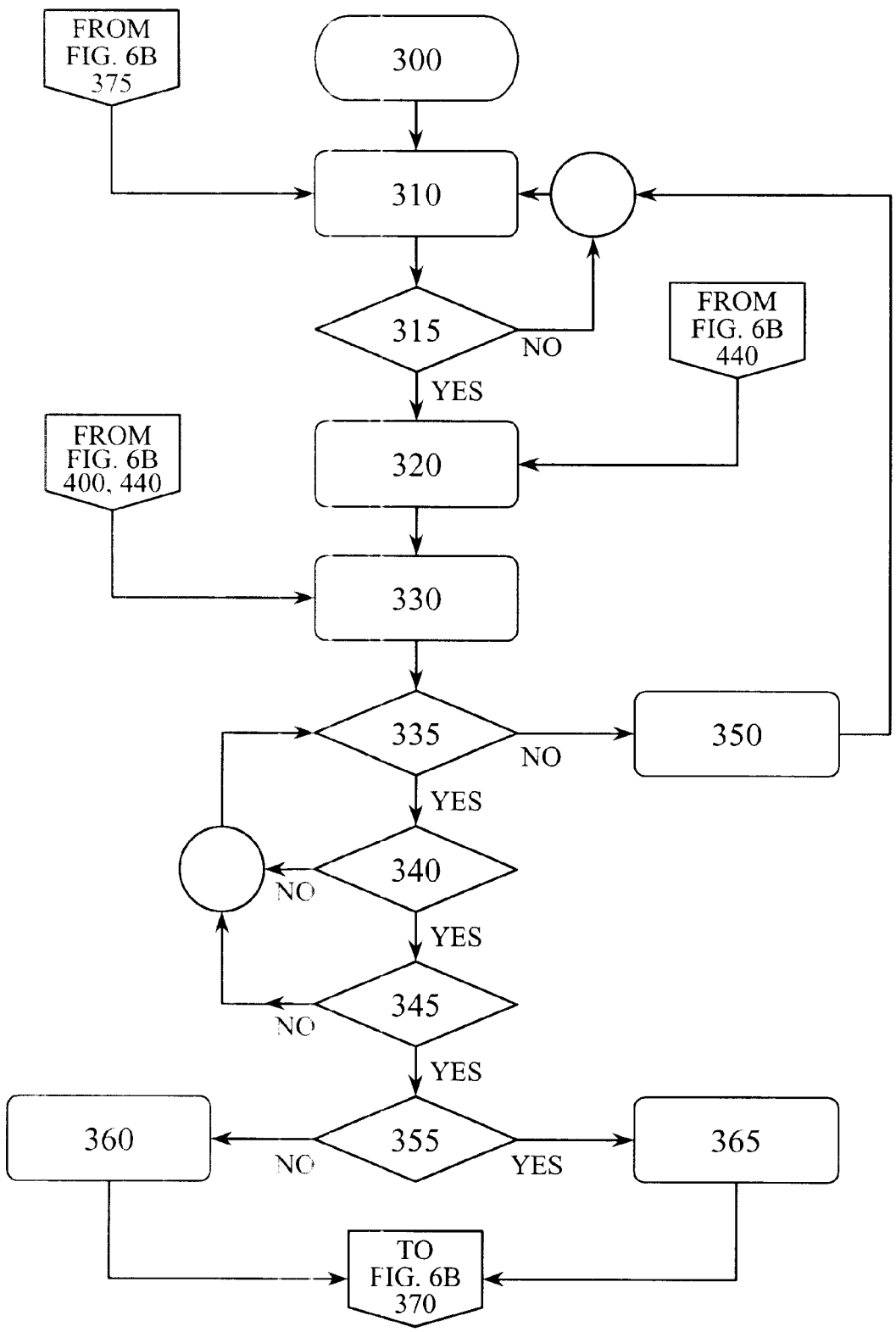
FIGS. 6A and 6B are functional descriptions of the method of operation of the therapeutic laser apparatus of the present invention.
Figure 6B:
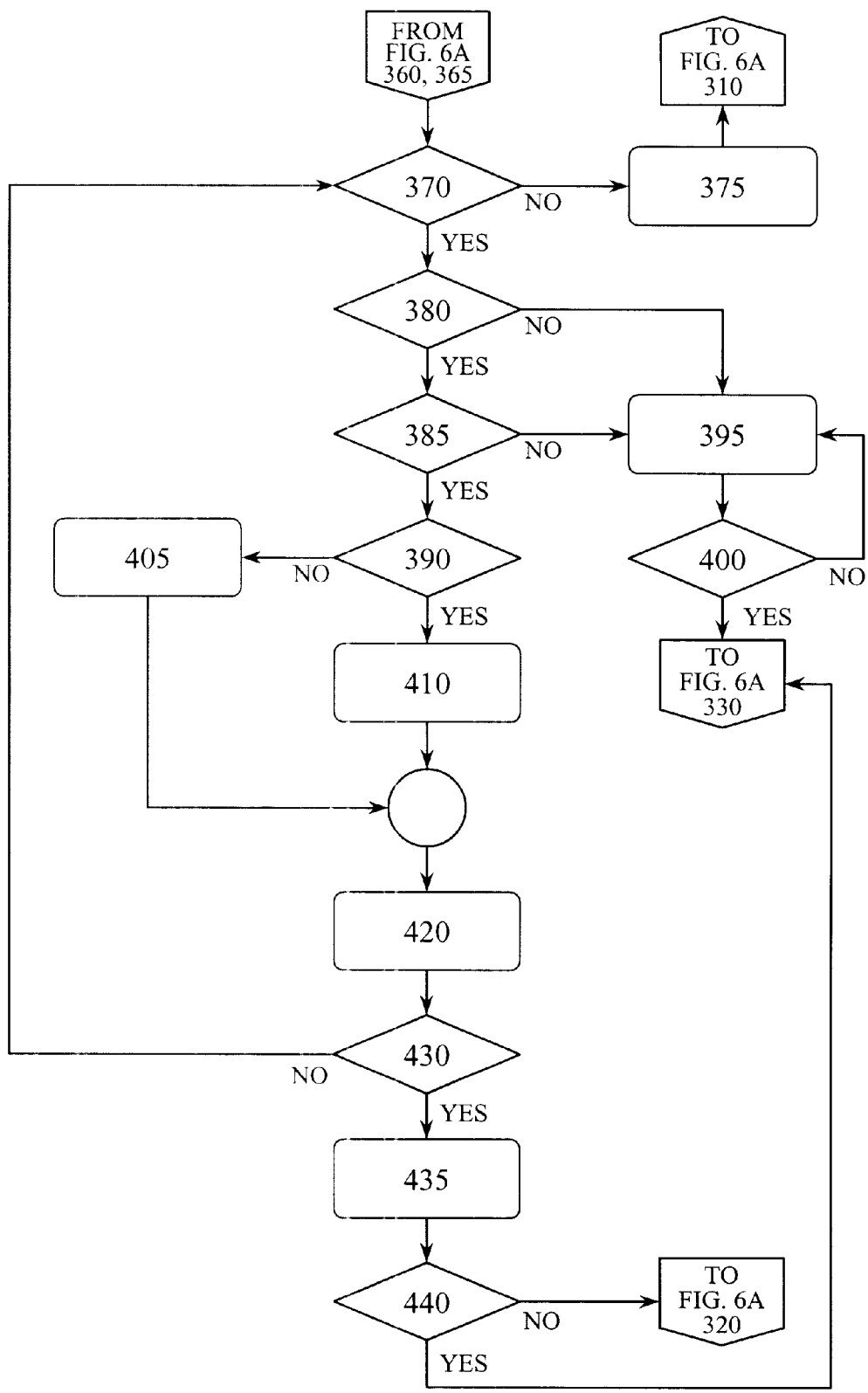

Referring now to FIGS. 1, 6A, and 6B, the device 10 is operated by first energizing the power switch 80 on the control panel 70. The preprogrammed logic of the controller 210 initiates a system self-test subroutine 300 and displays progress, system status, and operator welcome messages 310 on the LCDs 115, 120. The logic programmed into the controller 210 next scans the status 315 of the arming key switch 90. An operator's key must be inserted into the arming switch 90 before any of the laser radiation sources 165, 170 can be energized.

The controller continuously scans the arming switch 90 and automatically detects when the switch has been energized. Once energized, the controller 210 next executes a user prompt routine 320 that displays operator prompts on the LCDs 115, 120 requesting the desired parameter settings for the energy dosage in joules, power setting in watts per wand, pulse frequency (if any), and pulse width or duty cycle. After the desired parameters have been entered via the keypad 100, the controller 210 continues to execute routine 320 to compute the time required to accomplish the procedure according to the entered parameters. After the time computation is completed, routine 330 executes to energize the visible light and aiming laser radiation sources 170. At this point, the laser wands 125, 130 can be aimed because the visible wavelength laser beams are emitted from the wands. If the mode switch 95 has been adjusted to select single laser operation, then only one of the aiming laser radiation sources 170 will be energized. In alternative embodiments, although not shown in the figures, either an analog switch or a keypad 100 entry can be made to adjust the intensity of the aiming laser radiation sources 170, if needed.

After the aiming laser radiation sources 170 have been energized, routine 335 is executed to ensure the key switch 90 remains energized, routine 340 is executed to ensure that all access doors are closed, and routine 345 is executed to make sure the foot pedal 40 is depressed. If all safety checks do not pass, then control is returned to routine 335. If the key switch 90 is no longer energized, then the aiming laser radiation sources are de-energized by routine 350 and control passes back to the welcome message prompt routine 310. Also, although not reflected in the various figures, opening of the treatment room entry door during treatment also executes routine 350. However, if all safety checks pass, then routine 355 executes to check the mode switch 95. If single laser or dual laser operation is selected, then either routine 360 or 365, respectively, is executed to energize either one or both therapeutic laser radiation sources 165. If additional laser radiation sources are available, then the mode switch would be adjusted to establish which of the plurality of laser radiation sources were to be energized.

Once all of the selected lasers have been energized, routine 370 executes to check the key switch 90. If de-energized, control passes to routine 375 to de-energize all of the lasers 165, 170 and control passes to the welcome message prompt routine 310. Otherwise, routines 380, 385, and 390 execute to respectively check to ensure all access doors and panels remain closed, that the pedal 40 remains depressed, and to check if the mode switch 95 has been adjusted. If any of the cabinet doors or access panels have been opened, routine 395 executes to de-energize all of the laser radiation sources 165, 170. Although not reflected in the various figures, opening of the treatment room entry door during treatment also executes routine 395. The operator is then prompted by "pause-resume" routine 400, which executes and sends a message to either or both of the LCDs 115, 120, and, if desired, a signal to the audio emitter 170. The operator may respond to the prompts and alerts by depressing the resume switch 105, returning control to routine 330 to initiate the series of pre-energization safety checks. Similarly, if routine 385 determines that the foot pedal 40 is no longer depressed, control passes to the all lasers off routine 395 and then to the pause-resume routine 400.

If all doors and panels have not been opened and remain closed and the foot pedal remains depressed, then mode switch check routine 390 executes to poll the mode switch 95. If the switch 95 has been adjusted, then the second laser radiation source is accordingly energized by routine 405 or de-energized by routine 410. Operation control then proceeds to counter routine 420 which increments the time remaining for the procedure as calculated initially by routine 320. Control then passes to timer routine 430. If the duration of time needed to complete the procedure has passed, then routine 435 executes to de-energize all laser radiation sources 165, 170. The operator is queried by routine 440, which sends a signal to the audio emitter 170, if desired, and displays prompts on the LCDs 115, 120, to determine whether the therapeutic laser application procedure should be repeated. If not, control passes to the operator prompt routine 320. If the operator elects to repeat the procedure, then control is transferred to routine 330, and the above operations are repeated.

The present invention also includes a method for treatment of tissue. The method involves exposing the tissue to a plurality of radiation sources having a wavelength of between approximately 900 nm and approximately 1100 nm. More generally, the method of treatment of the present invention involves the exposure of the tissue to a plurality of converging beams of infrared radiation of between about 900 nm and 1100 nm. Any embodiment of the device of the present invention, including but not limited to those previously described, can be used to perform this method of treatment.

Figure 7:
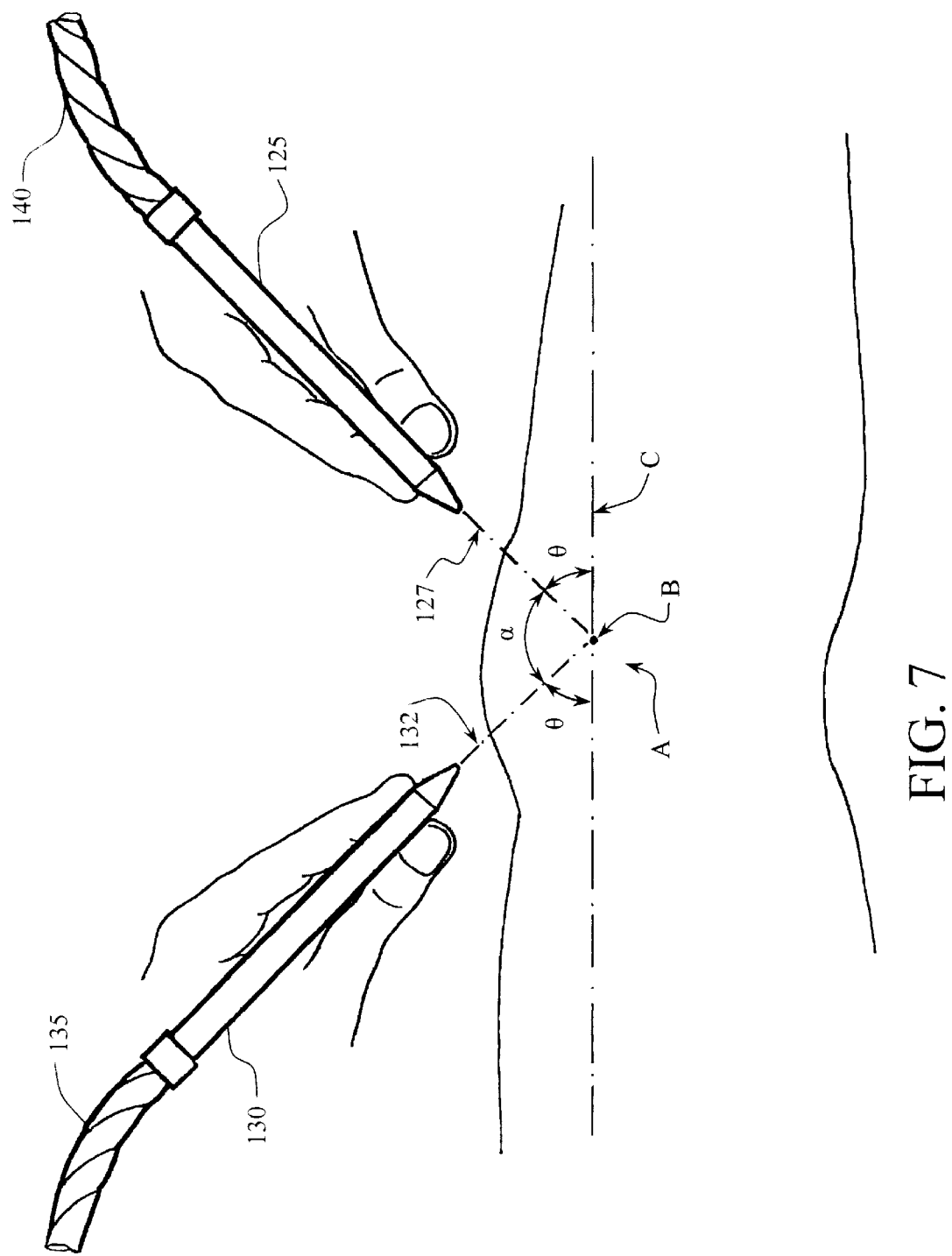
FIG. 7 is a side view of an embodiment of the laser wands of the apparatus of FIGS. 1 and 2, in enlarged scale, in operation and directed towards a human knee undergoing therapeutic biostimulation.

Referring next to FIG. 7, the operator hands are shown holding the laser wands 125, 130 above the biological tissue "A" to be treated. As shown, the wands 125, 130 are preferably positioned so the beams intersect at a region "B"

of the biological tissue "A" undergoing treatment. The wands 125, 130 are preferably oriented at an angle α (alpha) relative to each other and an angle θ (theta) to an imaginary, approximately horizontal reference line "C" passing through the tissue undergoing treatment so that the beams 127, 132 intersect. The intersection of the emitted infrared, treatment laser radiation significantly improves the absorption of the energy by the tissue at and proximate to the region or point of intersection "B" of the beams 127, 132. The operator preselects the region or regions to be treated and may vary the location of the intersection region "B" by adjusting the position and orientation of the wands 125, 130.

Obstacles to radiation penetration, such as oils or other substances on the surface of the skin, should be preferably removed before treatment because they may absorb, refract, and/or diffract the incident radiation, and thereby decrease radiation penetration. Because oils or other substances on the surface of the skin may cause absorption, fraction, reflection, and/or defraction of the wavelength of radiation, and thereby decrease radiation penetration, these obstacles should be removed before treatment.

Although not shown in the figures, the invention also contemplates an automatic positioning device configured to fixedly and/or changeably adjust the position and orientation of the wands 125, 130 relative to one another and relative to the biological tissue undergoing therapeutic laser treatment. The positioning device is configured to adjust position and orientation of the wands 125, 130 into an operative position with the emitted aiming and therapeutic laser beams having an intersection region within the biological tissue receiving the treatment similar to the description above and in FIG. 7. The positioning device may include an assembly operative to automatically vary the relative positions and orientation of the wands 125, 130 during the therapeutic laser application.

From the foregoing, it would be obvious to those skilled in the art that various modifications in the above described method and apparatus can be made without departing from the spirit and scope of the invention. Accordingly, the invention may be embodied in other specific forms without departing from the spirit or essential characteristics thereof. Present embodiments, therefore, are to be considered in all respects as illustrative and not restrictive, the scope of the invention being indicated by the appended claims rather than by the foregoing description, and all changes which come within the meaning and range of equivalency of the claims are therefore intended to be embraced thereby.

What is claimed is:

1. A biostimulation device, comprising:
   a) a laser apparatus including a plurality of variably focusable treatment laser wands each connected to (1) a first laser radiation source adapted to emit radiation having a power of between zero and approximately 2.0 watts, an energy of between about 1 joule and about 99 joules, and a wavelength of between approximately 900 nm and 1100 nm, and (2) a second radiation source adapted to emit visible light; and
   b) wherein the laser wands are adapted to be arranged in an operative position to emit the radiation incident to a region of biological tissue for a therapeutically effective length of time between approximately one and approximately sixty minutes.

2. A biostimulation device, comprising:
   a) a laser apparatus including a plurality of treatment laser wands each connected to a first laser radiation source adapted to emit radiation having a power of approximately between 1 and 10 watts, an energy of between about 1 joule and about 99 joules, and a wavelength of between approximately 900 nm and 1100 mn, and a second radiation source adapted to emit visible light; and
   b) wherein the laser wands are focusable and adapted to be arranged in an operative position to emit the radiation incident to a region of biological tissue for a therapeutically effective length of time.

3. A device for photobiostimulation of biological tissue, comprising:
   a) a first plurality of treatment radiation sources each providing a respective first radiation beam having a wavelength of between approximately 900 nm and approximately 1100 nm;
   b) a second plurality of aiming radiation sources each providing a respective second radiation beam having a wavelength of between approximately 400 nm and approximately 700 nm; wherein at least one first beam and one second beam concurrently pass through at least one of a plurality of fiber optic cables; and
   c) at least two wands each connected to a different one of the plurality of fiber optic cables, the wands including a variable collimator configured to establish the focus of the emanating coincident radiation beam;
   wherein the wands are adapted to be arranged in an operative position about the tissue such that the radiation beams emitted from each wand simultaneously pass approximately through a region located in the tissue.

4. The biostimulation device of claim 3, wherein the treatment and aiming radiation sources incorporate light emitting diode lasers.

5. The biostimulation device of claim 3, wherein the treatment radiation source emits radiation having a wavelength of approximately 980 nm.

6. The biostimulation device of claim 3, wherein the aiming radiation source emits radiation having a wavelength of between approximately 635 nm and approximately 640 nm.

7. The biostimulation device of claim 3, wherein at least one of the wands incorporates an adjustable collimator operative to vary the focus of the emitted radiation beam.

8. The biostimulation device of claim 3, wherein the treatment radiation source is configured to emit adjustably pulsed radiation wherein the pulses have a frequency of between approximately 0.1 cycles per second and approximately 100 cycles per second.

9. The biostimulation device of claim 3, wherein the treatment radiation source is configured to emit continuous wave radiation.

10. The biostimulation device of claim 3, wherein the treatment radiation source is configured to adjustably emit pulsed radiation wherein the pulse width is between approximately 0.1 percent and 100 percent.

11. The biostimulation device of claim 3, wherein the treatment radiation source is configured to adjust the power level of the emitted radiation to have a power of between zero and approximately 2.0 watts.

12. The biostimulation device of claim 3, wherein the treatment radiation source is configured to adjust the energy level of the emitted radiation to have a power of between approximately 1 joule and 99 joules.

13. The biostimulation device of claim 11 or 12, wherein the treatment radiation source is configured to adjust the duration of the therapeutic laser radiation treatment to between approximately 1 second and 3600 seconds.

14. A method for the treatment of tissue, comprising the steps of:
  a) providing at least two infrared laser treatment radiation sources having a wavelength of between approximately 900 nm and approximately 1100 nm;
  b) providing at least two sources of aiming laser radiation having a wavelength of between approximately 400 nm and approximately 700 nm;
  c) combining the radiation sources so that the radiation of each source is coincident;
  d) passing the coincident radiation through at least two optical fibers;
  e) providing at least two wands connected to the optical fibers that include a focusable collimator;
  f) arranging the wands such that the radiation emitted from the wands simultaneously passes through a region located within the tissue; and
  g) exposing the tissue to the laser radiation for a therapeutically effective period of time.

15. The method for the treatment of tissue of claim 14, wherein the treatment and aiming radiation sources incorporate light emitting diode lasers.

16. The method for the treatment of tissue of claim 14, wherein the treatment radiation source emits radiation having a wavelength of approximately 980 nm.

17. The method for the treatment of tissue of claim 14, wherein the aiming radiation source emits radiation having a wavelength of between approximately 635 nm and approximately 640 nm.

18. The method for the treatment of tissue of claim 14, wherein at least one of the wands incorporates an adjustable collimator operative to vary the focus of the emitted radiation beam.

19. The method for the treatment of tissue of claim 14, wherein the treatment radiation source is configured to emit adjustably pulsed radiation wherein the pulses have a frequency of between approximately 0.1 cycles per second and approximately 100 cycles per second.

20. The method for the treatment of tissue of claim 14, wherein the treatment radiation source is configured to emit continuous wave radiation.

21. The method for the treatment of tissue of claim 14, wherein the treatment radiation source is configured to adjustably emit pulsed radiation wherein the pulse width is between approximately 0.1 percent and 100 percent.

22. The method for the treatment of tissue of claim 14, wherein the treatment radiation source is configured to adjust the power level of the emitted radiation to have a power of between zero and approximately 2.0 watts.

23. The method for the treatment of tissue of claim 14, wherein the treatment radiation source is configured to adjust the energy level of the emitted radiation to have a power of between approximately 1 joule and 99 joules.

24. The method for the treatment of tissue of claim 22 or claim 23, wherein the treatment radiation source is configured to adjust the duration of the therapeutic laser radiation treatment to between approximately 1 second and 3600 seconds.

25. A system for photobiostimulation of biological tissue, comprising:
  a) a controller unit including a power supply and a control panel having operator input devices and output devices;
  b) the controller unit also including a first plurality of treatment radiation sources each providing a respective first radiation beam having a wavelength of between approximately 900 nm and approximately 1100 nm;
  c) the controller unit also including a second plurality of aiming radiation sources each providing a respective second radiation beam having a wavelength of between approximately 400 nm and approximately 700 nm; wherein at least one first radiation beam and one second radiation beam concurrently pass through at least one of a plurality of fiber optic cables; and
  d) at least two wands each connected to a different one of the plurality of fiber optic cables, the wands including a collimator configured to establish the shape of the emanating coincident radiation beams; wherein the wands are adapted to be arranged in an operative position about the tissue such that the radiation beams emitted from each wand simultaneously pass approximately through a region located in the tissue.

26. A device for photobiostimulation of biological tissue, comprising:
  a) a first plurality of treatment radiation sources each providing a respective first radiation beam having a wavelength of between approximately 900 nm and approximately 1100 nm;
  b) a second plurality of aiming radiation sources each providing a respective second radiation beam having a wavelength of between approximately 400 nm and approximately 700 nm; wherein at least one first beam and one second beam concurrently pass through at least one of a plurality of fiber optic cables; and
  c) at least two wands each connected to a different one of the plurality of fiber optic cables, at least one of the wands including a collimator configured to adjust the focus of the emanating radiation beam;
  wherein the wands are adapted to be arranged in an operative position about the tissue such that the radiation beams emitted from each wand simultaneously pass approximately through a region located in the tissue.

27. A device for photobiostimulation of biological tissue, comprising:
  a) a treatment radiation source providing a respective first radiation beam having a wavelength of between approximately 900 nm and approximately 1100 nm;
  b) a second aiming radiation source providing a respective second radiation beam having a wavelength of between approximately 400 nm and approximately 700 nm; wherein the first beam and second beam concurrently pass through a fiber optic cable; and
  c) a wand connected to the fiber optic cable, and including a collimator configured to adjust the focus of the emanating radiation beam;
  wherein the wand is adapted to be arranged in an operative position about the tissue such that the radiation beam emitted from the wand illuminates a region located in the tissue.

28. A biostimulation device, comprising:
  a) a laser apparatus including a plurality of treatment laser wands each including a collimator with an adjustable focus, the wands being connected to a laser radiation source adapted to emit radiation having a power of between zero and approximately 2.0 watts, an energy of between about 1 joules and about 99 joules, and a wavelength of between approximately 900 nm and 1100 nm; and
  b) wherein the laser wands are adapted to be arranged in an operative position to emit the radiation incident to a region of biological tissue for a therapeutically effective length of time.

29. A system for photobiostimulation of biological tissue, comprising:
   a) a controller unit including a power supply and a control panel having operator input devices and output devices;
   b) the controller unit also including a first plurality of treatment radiation sources each providing a respective first radiation beam having a wavelength of between approximately 900 nm and approximately 1100 nm;
   c) the controller unit also including a second plurality of aiming radiation sources each providing a respective second radiation beam having a wavelength of between approximately 400 nm and approximately 700 nm; wherein at least one first radiation beam and one second radiation beam concurrently pass through at least one of a plurality of fiber optic cables; and
   d) at least two wands each connected to a different one of the plurality of fiber optic cables, the wands including a collimator configured to adjust the shape of the emanating coincident radiation beams; wherein the wands are adapted to be arranged in an operative position about the tissue such that the radiation beams emitted from each wand simultaneously pass approximately through a region located in the tissue.

30. A method for the treatment of tissue, comprising the steps of:
   a) providing at least two infrared laser treatment radiation sources having a wavelength of between approximately 900 nm and approximately 1100 nm;
   b) providing at least two sources of aiming laser radiation having a wavelength of between approximately 400 nm and approximately 700 mn;
   c) combining the radiation sources so that the radiation of each source is coincident;
   d) passing the coincident radiation through at least two optical fibers;
   e) providing at least two wands, connected to the optical fibers, wherein at least one wand includes a collimator configured to adjust the shape of an emitted radiation beam;
   f) arranging the wands such that the radiation emitted from the wands simultaneously passes through a region located within the tissue; and
   g) exposing the tissue to the laser radiation for a therapeutically effective period of time.

* * * * *